United States Patent [19]

Hochstein

[11] Patent Number: 4,629,334

[45] Date of Patent: Dec. 16, 1986

[54] ENGINE AND TRANSMISSION OIL DEGRADATION AND TEMPERATURE MONITOR

[76] Inventor: Peter A. Hochstein, 2966 River Valley Dr., Troy, Mich. 48098

[21] Appl. No.: 723,809

[22] Filed: Apr. 16, 1985

[51] Int. Cl.$^4$ .................... G01N 25/00; G01N 33/28
[52] U.S. Cl. ........................... 374/103; 73/64
[58] Field of Search ............... 73/64, 304 R, 304 C, 73/292; 324/65 P; 374/142, 102, 103, 104, 105; 340/59, 618, 622, 620

[56] References Cited

U.S. PATENT DOCUMENTS

| | | | |
|---|---|---|---|
| 2,972,253 | 2/1961 | Benson | 374/302 |
| 3,398,578 | 8/1968 | Dozer | 73/304 R |
| 3,474,337 | 10/1969 | Petrick | 73/304 R |
| 3,482,440 | 12/1969 | Curwen | 374/103 |
| 3,735,638 | 5/1973 | Miller | 73/304 R |
| 3,910,118 | 10/1975 | Schittek et al. | 73/304 R |
| 4,007,629 | 2/1977 | Hochstein | |
| 4,027,534 | 6/1977 | Zimmerman | 324/65 P |
| 4,296,472 | 10/1981 | Sarkis | 73/304 C |
| 4,322,713 | 3/1982 | Duck et al. | 340/620 |
| 4,377,550 | 3/1983 | Tokarz | 73/304 R |
| 4,487,066 | 12/1984 | Pardi et al. | 73/304 C |
| 4,497,200 | 2/1985 | Tournier | 73/64 |
| 4,503,419 | 3/1985 | Kidd et al. | 73/292 |

Primary Examiner—Daniel M. Yasich
Attorney, Agent, or Firm—Harold W. Milton, Jr.

[57] ABSTRACT

An oil monitor assembly (20) comprising a support (22) for removable attachment to an oil reservoir, a first electrode (24, 24') extending from the support (22) for immersion in an oil in the reservoir and a second electrode (28) extending from the support (22) in spaced relationship to the first electrode (24, 24'). An electrical circuit (34) is supported by the support (22) and is in direct electrical contact with the electrodes (24, 24', 28) for measuring the resistance (RRP-29) of the oil over its operational temperature range including the very high resistance of the oil at very cold temperatures to provide a signal in the absence of conducting oil between (29) the first (24, 24') and second (28) electrodes. The electrical circuit (34) includes a degradation circuit (48) for measuring the resistivity of the oil due to contamination and degradation while compensating for changes in resistivity of the oil due to changes in temperature. The temperature-sensitive resistor (RTS-32) is supported by the support (22) and is responsive to oil in the reservoir. The electrical circuit (34) is responsive to the temperature-sensitive resistor (RTS-32) for providing a signal in response to a predetermined temperature sensed by the temperature-sensing resistor (RTS-32).

21 Claims, 3 Drawing Figures

ENGINE AND TRANSMISSION OIL DEGRADATION AND TEMPERATURE MONITOR

TECHNICAL FIELD

This invention relates to the monitoring of automotive engine and transmission oil to provide signals at predetermined oil conditions.

BACKGROUND

Service interval monitors for the automotive industry are relatively new and are used to optimally service motor oil, filters and other replacement parts on vehicles.

Such preventive service has historically been performed on an elapsed time or elapsed mileage basis. More recent cost-benefit analyses have shown, however, that such preventive maintenance based solely on elapsed time or mileage is not a good indicator of actual service requirements. A far better indicator of service needs are various engine and vehicle operating parameters such as: integrated time-temperature history of engine oil, speed-time histograms of engine or transmission, engine load vs. time data, and oil contamination criteria.

Various electronic instruments have been developed to differentially weight these parameters, sum them according to a particular transfer function, establish permissible limits for the measured variables, and then alert the vehicle operator if these limits are exceeded.

More cost effective approaches have been developed wherein the service interval (which in automotive use is primarily the oil change interval) is determined by modeling (mathematically) the degradation of motor oil. The principal parameters affecting the degradation of motor oil are, time at temperature ($t.e^{kt}$) and the "contamination" factors. An exemplary system is disclosed in U.S. Pat. No. 4,007,629 in the name of Peter A. Hochestein.

Even the best service interval devices, electronic or mechanical, are not able to accurately determine the critically important lubricity of oil; either in an engine or automatic transmission. Contamination of engine oil by water soluble acids, water, particulate matter (dust or carbon) and oil degradation by-products severely affects the ability of the motor oil to lubricate, cool, and protect critical engine parts. Contamination of automatic transmission fluid by particulates, water, and other foreign matter, can also affect the mechanical function of mechanism, and in fact, cause damage to the precision mechanical valve body components in the hudraulic servo controls.

While the actual process of oil or transmission fluid degradation is different in an engine (heat, blow-by, etc) and in an automatic transmission (primarily thermal decomposition), the requirement to continually audit the fluid medium is the same.

Mineral, petroleum based motor oils, synthetic ester motor oils, and hydraulic fluid experimental data suggest that while the initial resistance of these oils is variable, the general behavior with temperature is similar, and follows an exponential curve.

Contamination of these fluids in use, changes the initial resistivity at a given temperature. However, the behavior relating to decreases in resistivity with increasing temperature is still valid.

Samples of used motor oil exhibiting decreases in resistivity as a function of usage confirm that contaminants or degradation of the oil base itself slowly increase the conductivity of the fluid.

Naturally, the effect of temperature on the resistivity of the fluid must be taken into account, if a true measure of resistivity change with use is desired. Factoring out the apparent change in resistivity due to temperature is critical because the slope of temperature dependence is greater than the slope of use (and contamination) dependence over the typical engine oil operating temperature range.

SUMMARY OF THE INVENTION AND ADVANTAGES

An oil monitor comprising; support means for removable attachment to an oil reservoir and a first outer electrode extending from said support means for immersion in oil in the reservoir. The first electrode is tubular and has perforations spaced circumferentially thereabout and axially therealong. A second inter electrode extends from the support means coaxially within and spaced from the first electrode with electrical insulation means spacing the second electrode within the first electrode. An electrical circuit means is supported by the support means and is in direct and immediate electrical contact with the electrodes for measuring the resistance of the oil over its operational temperature range including the very high resistance of the oil at very cold temperatures to provide a signal in the absence of conducting oil between the first and second electrodes.

The oil degradation monitor, described herein, senses the change in resistivity of the monitored fluid due to contamination or degradation. The normally occurring change of resistivity with temperature is disregarded by means of a temperature compensation circuit. Essential components required for the degradation monitoring function may also be used to sense an over-temperature condition, and/or a low fluid condition.

DESCRIPTION OF THE INVENTION

Figure 1:
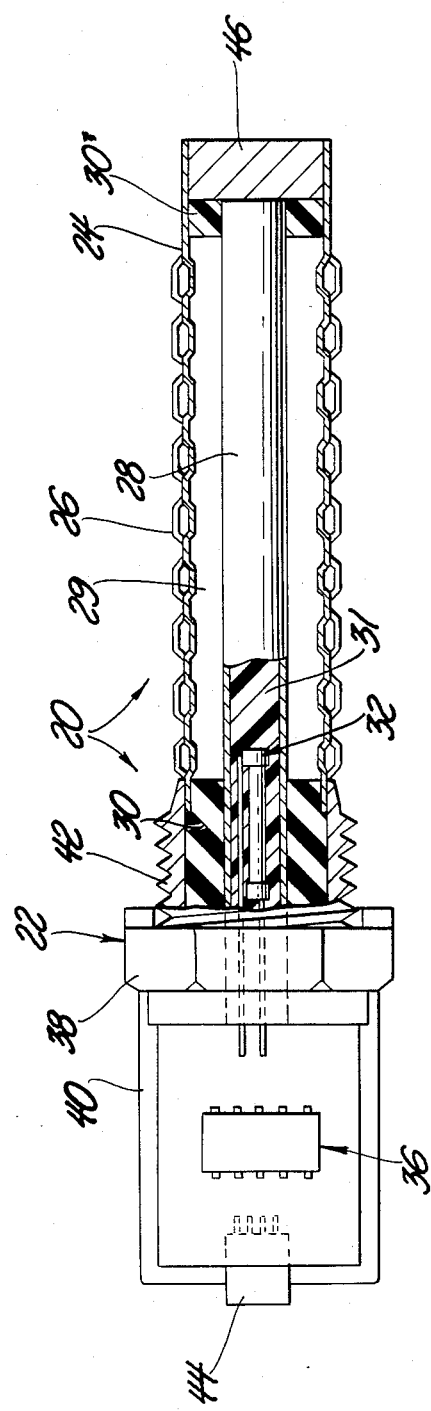
FIG. 1 is a side elevational view partially broken away and in cross section of an oil monitor assembly constructed in accordance with the instant invention.

An oil monitor assembly constructed in accordance with the subject invention is generally shown at 20 in FIG. 1. The assembly 20 includes support means generally indicated at 22, for removable attachment to an oil reservoir. An outer first electrode 24, 24' extends from the support means 22 for immersion in oil in the reservoir. The first electrode 24, 24' is tubular and has perforations 26, 26' spaced circumferentially thereabout and axially therealong. An inter-second electrode 28 extends from the support means 22 coaxially within and spaced 29 from the first electrode 24, 24'. An electrical insulation means 30 spaces the second electrode 28 within the first electrode 24, 24'. The second electrode 28 is also tubular.

The assembly also includes temperature-sensing means generally indicated at 32 and disposed within the second electrode 28. A heat conducting potting material 31 fills the electrode 28 and encapsulates the temperature-sensing means 32.

Figure 2:
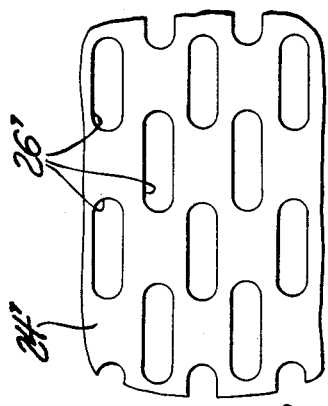
FIG. 2 is a fragmentary plan view of an alternative electrode for use in the assembly of FIG. 1.

An electrical circuit means 34 on a printed circuit board 36 is the support means 22 for providing a signal in response to a predetermined temperature sensed by the temperature-sensing means 32 and for providing a signal in the absence of oil between the first 24, 24' and second 28 electrodes and for providing a signal in response to a predetermined degradation of the oil. The support means 22 includes a nut 38 and a housing 40 attached to one side of the nut 38 and a threaded skirt 42 extending from the other side of the nut 38. The electrical insulation means 30 is disposed between the skirt 42 and the second electrode 28. The first electrode 24 is supported within and extends from the skirt 42. A second electrical insulation means 30' is disposed annularly between the first and second electrodes at the distal ends thereof. The first or outer electrode 24 is sufficiently perforated to prevent retention of oil therein by capillary action. The outer electrode 24 may be made of expanded metal as illustrated in FIG. 1 or include elongated oval or eliptical holes as illustrated at 24' in FIG. 2. In any case, the hole or void area should be at least twenty-five percent (25%) of the total electrode cylinders. A connector means 44 is disposed on the housing for connection to opposed voltage supplies whereby the support means 22 may be attached to a nonelectrically conductive member. In other words, the reservoir into which the assembly 20 is inserted may be plastic. A magnet means 46 is attached to the end of the first electrode 24 for attracting contaminants in the oil. Specifically, the magnet is disposed within the end of the outer or first electrode 24. The first electrode 24, 24' is made of nonmagnetic and noncorrosive material.

The electrical circuit means 34 is supported by the support means 22 to be in direct electrical contact with the electrodes 24, 28 for measuring the resistance of the oil over its operational temperature range including the very high resistance of the oil at very cold temperatures to provide a signal in the absence of conducting oil between the first 24, 24' and second 28 electrodes. In other words, there is very little electrical distance between the sensing circuit 34 and the electrodes 24, 28. They are supported in close spaced relationship to one another on the same platform.

The electrical circuit means 34 includes a CMOS comparator or compensating ampifier I.C.1A and a plurality of coupled resistances R7, R8, R9 and R10 defining an operational amplifier. This operational amplifier along with a bridge circuit comprising resistors R2, R3, R4 and RTS define a temperature compensation circuit 46. Resistor RTS is a temperature compensating resistor defining a temperature-sensitive means 32. The temperature comparator I.C.1B and the temperature-sensitive resistance RTS coupled thereto provide an over temperature signal when the temperature-sensitive resistance RTS exceeds a predetermined value. The temperature comparator I.C.1B, light-emitting diode L1, resistances R1, R5 and R12, and zener diode Z1 comprise an over temperature alarm circuit 56. The temperature-sensitive means 32 i.e., resistor RTS, supported by the support means 22 is responsive to oil temperature in the reservoir and the electrical circuit means 34 is responsive to the temperature-sensitive means 32 for providing a signal in response to a predetermined temperature sensed by the temperature-sensing means 32.

The electrical circuit means 34 also includes degradation circuit means or degraded fluid alarm circuit 48 for measuring the resistivity of the oil due to contamination and degradation while compensating for changes in resistivity of the oil due to changes in temperature. The electrical circuit means further comprises a low fluid alarm circuit 50 including a low level comparator I.C.2B having high input impedance coupled with a plurality of resistors R13, R16, R17 and R19 to define an operational amplifier or comparator coupled immediately across the first 24 and second 28 electrodes for providing a low level signal in the absence of conductive oil extending between the electrodes. A plurality of bridge resistors R2, R3, R4 are coupled with the temperature-sensitive resistance 32 (RTS) to define a bridge. The operational amplifier configured by temperature-compensating amplifier I.C.1A and the coupled resistors R7, R8, R9 and R10 amplify the differential output of the bridge and establish an output voltage which varies with the characteristic change in resistivity due to change in temperature of the oil 29. A degradation limit comparator I.C.2A is respectively responsive to the temperature-compensating amplifier I.C.1A and the fluid resistance signal developed by RRP for providing a degradation signal in response to a predetermined minimum level of resistivity of the oil 29.

Positive and negative power supply leads 52 and 54 are included, the positive lead 52 being twelve volts are used in most vehicles. A first resistor R1 extends between the positive lead 52 and a fifth input pin 5, to the temperature comparator I.C.1B. The second and third and fourth resistors R2, R3 and R4 which define the bridge resistors coupled to said temperature-responsive resistance RTS have a differential output which is applied to the second and third input pins 2, 3 of the compensating amplifier I.C.1A. A fifth resistor R5 is disposed between the bridge and the fifth input 5 to the temperature comparator I.C.1B to define a divider with the first resistor R1. A diode Z1 is coupled between the negative lead 54 and the juncture 56 between the first resistor R1 and the bridge. A sixth resistor R6 is disposed between the zener diode Z1 and the positive lead 52 for limiting current to act with the zener diode Z1 to establish a reference voltage for the bridge and the divider. The seventh and eighth and ninth and tenth and eleventh resistors R7, R8, R9, R10 and R11 configure compensating amplifier I.C.1A as an operational amplifier. A first capacitor C1 is coupled with the output pin 1 of the compensating amplifier I.C.1A to provide output stability. The fifth input pin 5 of the temperature comparator I.C.1B is coupled through the fifth resistor R5 and the seventh resistor R7 to the second input pin 2 of the compensator amplifier I.C.1A. A sixth input pin 6 of the temperature comparator I.C.1B is coupled through the eighth resistor R8 to a third input pin 3 of the compensator amplifier I.C.1A. A first light-emitting diode L1 is coupled to the output pin 7 of the temperature comparator I.C.1B for illumination whenever temperature-sensitive resistor RTS exceeds a predetermined resistance. A twelfth resistor R12 at the output of the light-emitting diode L1 limits current therethrough. The fifth resistance R5 is adjustable for setting the predetermined temperature. The thirteenth and fourteenth and fifteenth, sixteenth and seventeenth resistors R13, R14, R15, R16 and R17 are coupled with the first 24 and second 28 electrodes and the low fluid level comparator I.C.2B. The fourteenth and fifteenth resistors R14 and R15 define a divider string for applying voltage through the sixteenth resistor R16 to the first 24 and second 28 electrodes. The thirteenth and seventeenth resistors R13 and R17 define a divider applied to a fifth input pin 5 of the low fluid level comparator I.C.2B. A sixth input pin 6 of low fluid level comparator I.C.2B is coupled to sense the voltage across 29 the first 24 and second 28 electrodes. A second capacitor C2 presents a low impedance path to the negative lead 54 for alternating currents. A nineteenth resistor R19 is coupled between the fifth input pin 5 and the output pin 7 of the low fluid level comparator I.C.2B for providing hysteresis. A second light-emitting diode L2 and a twentieth resistor R20 are in series between the output pin 7 of the low fluid level comparator I.C.2B and the positive supply lead 52. A second input pin 2 to the degradation comparator I.C.2A is coupled to the output pin 1 of the compensating comparator I.C.1A and a third input pin 3 to degradation comparator I.C.2A is coupled to the sixth input pin 6 to the low fluid level comparator I.C.2B. A third capacitor C3 is disposed between the positive lead 52 and the seventeenth resistor R17 for power supply decoupling. A third light-emitting diode L3 and twenty-first resistor R21 are in series between the output pin 1 of the degradation comparator I.C.2A and the positive supply lead 52.

The resistivity probe shown in FIG. 1 would normally be mounted horizontally (as shown) in an engine oil pan or transmission fluid reservoir. This device is constructed of corrosion-resistant perforated metal, so as to allow viscous fluid to readily flow into or out of the sensing space between the coaxial cylinders.

The temperature-sensing means 32 or resistor RTS is conveniently located within the central electrode tube 28. The optional ceramic magnet 46 located near the probe electrode will scavenge ferrous contaminants carried by the fluid. Such contaminating particles could short-circuit the sensing probe, rendering it ineffective.

Accurate measurement of the volume resistivites of motor oils and transmission fluids, which are in the range of $10^9$ to $10^{11}$ Ohm-cm, is not simple. Typically, resistances to be measured will be on the order of $10^9$ Ohms, because the sensing area of practical probes is limited. These high resistances are normally measured with a high voltage (250 volt) measuring instrument, so that the current levels become manageable. At test voltages of 150 volts (d.c.) the measured currents are still less than $1 \times 10^{-6}$ Ampere, for a probe with a sensing area of about 20 sq. cm, at room temperature. For operation at the nominal 12 volt d.c. levels available in cars, the currents to be measured drop to the tens of nanoamperes ($10^{-9}$). Reliable cost effective sensing of these very low currents in the automotive environment, can only be accomplished by using the newer CMOS integrated comparators and operational amplifiers.

Figure 3:
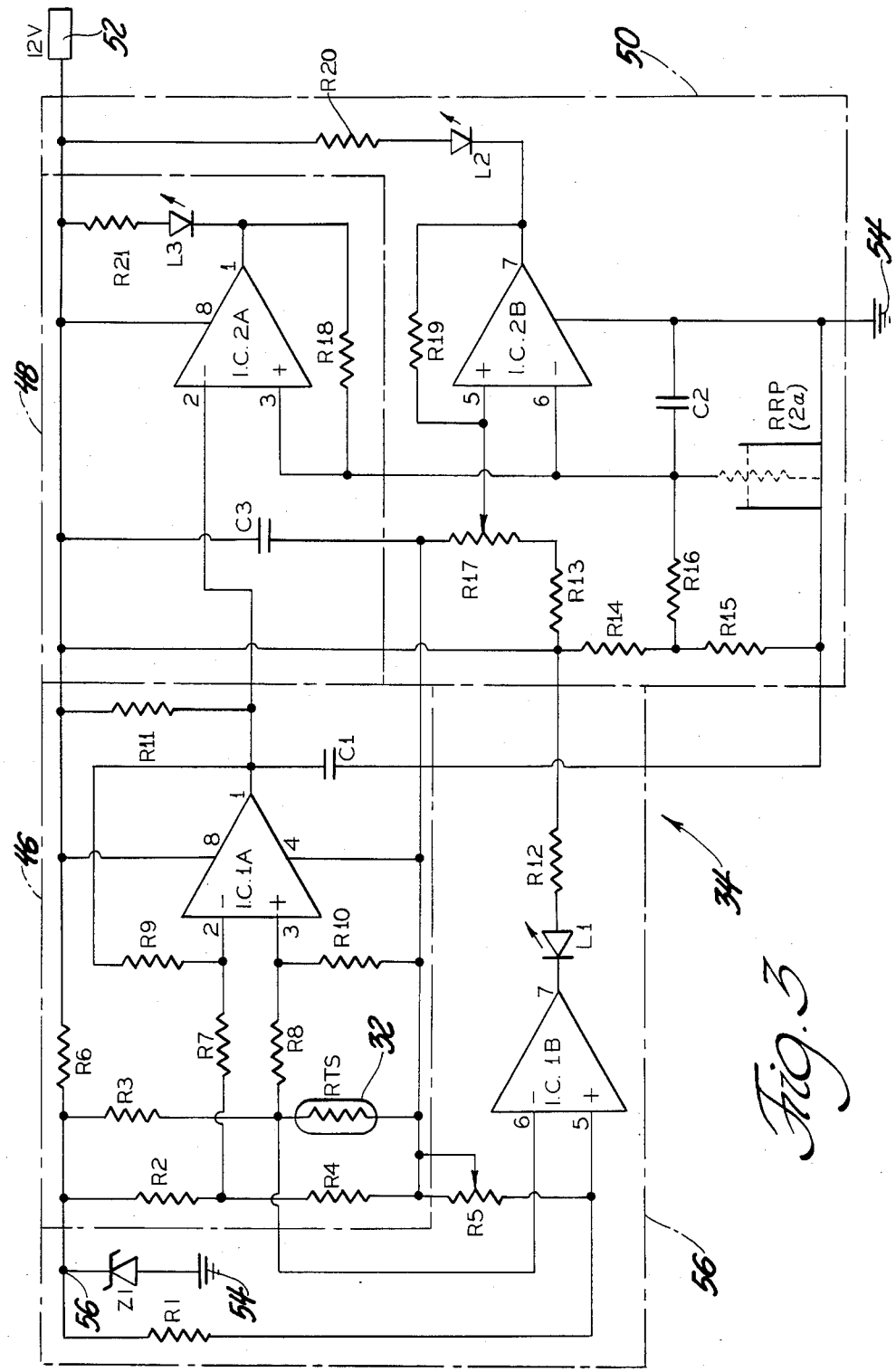
FIG. 3 is an electrical diagram of the circuit used in the assembly of FIG. 1.

The electronic circuitry of FIG. 3 is conveniently mounted to the sensing probe and is encapsulated in an imprevious potting medium. Close mounting of the sensing electronics increases system reliability by obviating the need for high impedance cables and the attendant difficulties (moisture sensitivity leakage, sensitivity to electrical interference, etc.)

OPERATION OF THE INVENTION

The oil degradation monitor system consists of the four functional blocks: (1) temperature compensation circuit 46; (2) degraded fluid alarm circuit 48; (3) low fluid alarm circuit 50; (4) over-temperature alarm circuit 56.

The differential output of measuring bridge R2, R3, R4 and RTS is amplified by CMOS comparator I.C.1A configured by the resistances R7, R8, R9, R10 as an operational amplifier with a gain of 4.57. The pull-up resistor R11 converts the CMOS comparator I.C.1A to an operational amplifier with output stability insured by the capacitor C1. This voltage gain, in conjunction with the positive 4000 part per million temperature coefficient of the Balco temperature sensing resistor RTS, establishes an output voltage at pin 1 of I.C.1A which is essentially linear and closely follows the temperature versus resistivity characteristic of transmission fluid. For example, the voltage developed by resistivity probe RRP (29) at pin 6 of I.C.2B is 0.90 volts at 50° C. and 3.60 volts at 150° C. in type "F" transmission fluid. The temperature compensation circuit 46 develops corresponding variable setpoint programming voltages (0.90 volts @ 50° C. to 3.60 volts @ 150° C.) with the same slope.

The over-temperature alarm circuit 56, and specifically the setpoint limit comparator I.C.1B, develops an alarm output whenever the temperature of the sensing resistor RTS 32 exceeds a predetermined resistance value (typically at 140° C.=. The integrated circuit I.C.1B, is a CMOS comparator which derives its setpoint voltage through divider resistances R1, R5, with one resistance R5 adjustable for precise temperature setting. The measured voltage across RTS is compared to the setpoint voltage at pin 5 of I.C.1B. The light-emitting diode L1 is illuminated whenever the temperature-sensitive resistance RTS voltage at pin 6 exceeds the setpoint voltage established at pin 5 of I.C.1B. Resistor R12 is the light-emitting diode L1 current limiting resistor. The current limiting resistor R6 in conjunction with zener diode Z1 establishes a 7.0 volt reference voltage for the bridge and the setpoint divider. Hysteresis is provided by the thermal inertia of the temperature-responsive sensing resistor RTS.

The low fluid level alarm circuit 50 includes the high input impedance setpoint comparator I.C.2B. Approximately two-thirds the voltage supply 52 is developed by divider string R14, R15 and applied to the resistivity sensing probe RRP (29) through resistor R16. The voltage developed across probe or electrodes 24, 28 (RRP-29) is, of course, a function of the actual resistance of (RRP-29), which varies with temperature, contamination, degradation, and fluid height. A predetermined acceptance level is established by divider resistors R13 and R17 and impressed on pin 5 of comparator I.C.2B. The inverting input of I.C.2B at pin 6 senses the voltage developed across the probe or electrodes 24, 28 (RRP-29). Should the fluid level drop below a predetermined point in the RRP-29 resistivity probe, the voltage at pin 6 increases. When the voltage at pin 6 exceeds the voltage set at pin 5, the comparator I.C.2B changes state, illuminating light-emitting diode L3 signalling a low fluid condition. As the input impedance to the CMOS comparator I.C.2B is in excess of 1.5 Terra Ohms, it does not load the measuring probe to any significant degree. The capacitor C2 at the op-amp input presents a low impedance path to ground for a.c. currents which might be inductively or capacitively coupled to the probe. Hysteresis is provided by resistor R19 so that splashing of the fluid in RRP or the space 29 between the electrodes 24 and 28 will not cause intermittent triggering of the light-emitting diode L3.

The degradation limit comparator I.C.2A derives a temperature variable setpoint voltage from I.C.1A. This varying setpoint is applied to the inverting input of the degradation limit comparator I.C.2A, while the noninverting input is developed across the resistivity probe RRP i.e., space 29 between electrodes 24 and 28. At any given temperature, whenever the resistivity of the fluid falls below a minimum acceptable level (voltage at pin 2 of I.C.2A), the output of comparator I.C.2A changes state and illuminates light-emitting diode L2.

The capacitor C3 is used for power supply decoupling while resistors R20 and R21 are used to limit the respective currents in light-emitting diodes L2 and L3.

In a preferred circuit, the following components may be used:

COMPONENTS

RTS: Temp sensing Resistor, Balco 1K Ohm, 0.25 W., T.C.+4000 PPM
RRP: Resistivity Probe Resistor; Nom. $7 \times 10^8$ Ohm
R1: 100K Ohm Resistor
R2: 20K Ohm Resistor
R3: 2K Ohm Resistor
R4: 9.6K Ohm Resistor
R5: 20K Ohm Potentiometer
R6: 100 Ohm Resistor
R7: 100K Ohm Resistor
R8: 100K Ohm Resistor
R9: 457K Ohm Resistor
R10: 457K Ohm Resistor
R11: 10K Ohm Resistor
R12: 470 Ohm Resistor
R13: 330K Ohm Resistor
R14: 1M Ohm Resistor
R15: 2.2M Ohm Resistor
R16: 20M Ohm Resistor
R17: 750K Ohm Potentiometer
R18: 27M Ohm Resistor
R19: 27M Ohm Resistor
R20: 470 Ohm Resistor
R21: 470 Ohm Resistor
Z1: 7.0 volt Zener diode
L1-L3: L.E.D.
I.C.1,2: CMOS Comparator; RCA CA3290E
C1: Capacitor; 0.1 Microfarad
C2: Capacitor; 0.01 Microfarad
C3: Capacitor; 10 Microfarad The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. An oil monitor assembly (20) comprising; support means (22) for removable attachment to an oil reservoir, an outer first electrode (24, 24') extending from said support means (22) for immersion in oil in the reservoir, said first electrode (24, 24') being tubular and having perforations (26, 26') spaced circumferentially thereabout and axially therealong, an inner second electrode (28) extending from said support means (22) coaxially within and spaced (29) from said first electrode (24, 24'), and electrical insulation means (30, 30') spacing said second electrode (28) within said first electrode (24, 24'), said second electrode (28) being tubular, and including temperature sensing means (RTS-32) disposed within said second electrode (28).

2. An assembly as set forth in claim 1 including heat conducting potting material (31) encapsulating said temperature sensing means (RTS-32) within said second electrode (28).

3. An assembly as set forth in claims 1 including electrical circuit means (34) housed (40) in said support means (22) for providing a signal in response to a predetermined temperature sensed by said temperature sensing means (RTS-32) and for providing a signal in the absence of oil between (29) said first (24, 24') and second (28) electrodes.

4. An assembly as set forth in claim 1 including electrical circuit means (34) housed (40) in said support means (22) for providing a signal in response to a predetermined temperature sensed by said temperature sensing means (RTS-32) and for providing a signal in the absence of oil between (29) said first (24, 24') and second (28) electrodes and for providing a signal in response to a predetermined degradation of the oil.

5. An assembly as set forth in claim 1 wherein said support means (22) includes a nut (38) and a housing (40) attached to one side of said nut (38) and a threaded skirt (42) extending from the other side of said nut (38), said electrical insulation means (30) being disposed between said skirt (42) and said second electrode (28), said first electrode (24, 24') supported within and extending from said skirt (42).

6. An assembly as set forth in claim 1 wherein said first electrode (24, 24') is sufficiently perforated (26, 26') to prevent retention of oil therein by capillary action.

7. An assembly as set forth in claim 1 including connector means (44) on said housing (40) for connection to opposed voltage supplies (52, 54) whereby said support means (22) may be attached to a nonelectrically conductive member.

8. An assembly as set forth in claim 1 including a magnet means (46) attached to said first electrode (24, 24') for attracting contaminants in the oil.

9. An assembly as set forth in claim 1 wherein said first electrode (24, 24') is made of nonmagnetic material.

10. An assembly as set forth in claim 1 wherein said first electrode (24, 24') is made of nonmagnetic and noncorrosive material.

11. An assembly as set forth in claim 1 wherein said first electrode (24) is made of an expanded steel tube.

12. An oil monitor assembly (20) comprising; support means (22) for removable attachment to an oil reservoir, a first electrode (24, 24') extending from said support means (22) for immersion in an oil in the reservoir, a second electrode (28) extending from said support means (22) in spaced relationship to said first electrode (24, 24'), electrical circuit means (34) supported by said support means (22) and in direct electrical contact with said electrodes (24, 24', 28) for measuring the resistance (RRP-29) of the oil between said first (24, 24') and second (28) electrodes, said electrical circuit means (34) including degradation circuit means (48) for measuring the resistivity of the oil due to contamination and degradation, a temperature compensation circuit (46) for measuring the change in resistivity of the oil due to changes in temperature of the oil, an over temperature alarm circuit (56) for providing an over temperature signal when the temperature of the oil exceeds a predetermined value, and a low fluid alarm circuit (50) for providing a low level signal in the absence of conducting oil between (29) said first (24, 24') and second (28) electrodes.

13. An assembly as set forth in claim 12 wherein said electrical circuit means (34) includes a low fluid level comparator, (I.C.2B) having high input impedance coupled with a plurality of resistors (R13, R16, R17 and R19) to define a comparator coupled immediately to said first (24, 24') and second (28) electrodes for providing a low level signal in the absence of conducting oil extending between said electrodes, and a temperature comparator (I.C.1B) and a temperature sensitive resistance (RTS) coupled thereto for providing an over temperature signal when said temperature-sensitive resistance exceeds a predetermined value.

14. An assembly as set forth in claim 13 wherein said electrical circuit means (34) includes a plurality of bridge resistors (R2, R3 and R4) coupled with said temperature-sensitive resistance RTS to define a bridge and an operational amplifier configured by a compensating amplifier (I.C.1A) and coupled resistors (R7, R8, R9, R10) to amplify the differential output of said bridge and establish an output voltage which varies with the characteristic change in resistivity due to change in temperature of the oil and a degradation limit comparator (I.C.2A) respectively responsive to said compensating amplifier (I.C.1A) and said low fluid level comparator (I.C.2B) for providing a degradation signal in response to a predetermined minimum level of resistivity of the oil.

15. An oil monitor assembly (20) comprising; support means (22) for removable attachment to an oil reservoir, a first electrode (24, 24') extending from said support means (22) for immersion in an oil in the reservoir, a second electrode having a sensor and (28) extending from said support means (22) in spaced relationship to said first electrode (24, 24'), electrical circuit means (34) supported by said support means (22) and in direct electrical contact with said electrodes (24, 24', 28) for measuring the resistance (RRP-29) of the oil between said first electrode (24, 24') and said second electrode (28) over its operational temperature range including the very high resistance of the oil at very cold temperatures to provide a signal in the absence of conducting oil between (29) said first (24, 24') and second (28) electrodes.

16. An assembly as set forth in claim 15 wherein said electrical circuit means (34) includes degradation circuit means (48) for measuring the resistivity of the oil due to contamination and degradation while compensating for changes in resistivity of the oil due to changes in temperature.

17. An assembly as set forth in claim 15 including temperature-sensitive means (RTS-32) supported by said support means (22) and responsive to oil in the reservoir, said electrical circuit means (34) being responsive to said temperature-sensitive means (RTS-32) for providing a signal in response to a predetermined temperature sensed by said temperature-sensing means (RTS-32).

18. An assembly as set forth in claim 15 or 12 wherein said electrical circuit means (34) includes a CMOS amplifier (I.C.1A) and a plurality of coupled resistances (R7, R8, R9 and R10) defining an operational amplifier.

19. An assembly as set forth in claim 15 wherein said electrical circuit means (34) includes a low fluid level comparator (I.C.2B) having high input impedance coupled with a plurality of resistors (R13, R16, R17 and R19) to define a comparator coupled immediately to said first (24, 24') and second (28) electrodes for providing a low level signal in the absence of conductive oil extending between said electrodes, and a temperature comparator (I.C.1B) and a temperature-sensitive resistance (RTS) coupled thereto for providing an over temperature signal where said temperature-sensitive resistance exceeds a predetermined value.

20. An assembly as set forth in claim 19 wherein said electrical circuit means (34) includes a plurality of bridge resistors (R2, R3 and R4) coupled with said temperature-sensitive resistance (RTS) to define a bridge and an operational amplifier configured by a compensating amplifier (I.C.1A) and coupled resistors (R7, R8, R9 and R10) to amplify the differential output of said bridge and establish an output voltage which varies with the characteristic change in resistivity due to change in temperature of the oil and a degradation limit comparator (I.C.2A) respectively responsive to said compensating amplifier (I.C.1A) and said low fluid level comparator (I.C.2B) for providing a degradation signal in response to a predetermined minimum level of resistivity of the oil.

21. An assembly as set forth in claim 20 or 14 including positive (52) and negative (54) power supply leads, a first resistor (R1) between said positive lead (52) and a fifth input (5) to said temperature comparator (I.C.1B), said second and third and fourth resistors (R2, R3 and R4) coupled to said temperature-responsive resistance (RTS) to define the bridge having a differential output applied to second and third inputs (2, 3) of said compensating amplifier (I.C.1A), a fifth resistor (R5) disposed between said bridge and said fifth input (5) to said temperature comparator (I.C.1B) to define a divider with said first resistor (R1), a Zener diode (Z1) coupled between said negative lead (54) and said juncture between said first resistor (R1) and said bridge, a sixth resistor (R6) disposed between said Zener diode (Z1) and said positive lead (52) for limiting current to act with said zener diode (Z1) to establish reference voltage for said bridge and said divider, seventh and eighth and ninth and tenth and eleventh resistors (R7, R8, R9, R10 and R11) to configure an operational amplifier I.C.1A, a first capacitor (C1) coupled with the output (1) of said compensating comparator (I.C.1A) to provide output stability, said fifth input (5) of said temperature comparator (I.C.1B) coupled through said fifth resistor (R5) and said seventh resistor (R7) to the second input (2) of said compensator amplifier (I.C.1A), a sixth input (6) to said temperature comparator (I.C.1B) coupled through said eighth resistor (R8) to a third input (3) to said compensator amplifier (I.C.1A), a first light-emitting diode (L1) coupled to the output (7) of said temperature comparator (I.C.1B) for illumination wherever temperature-sensitive resistor (RTS) exceeds a predetermined resistance, a twelfth resistor (R12) at the output of said light-emitting diode (L1) for limiting current therethrough, said fifth resistance (R5) being adjustable for setting said predetermined temperature, thirteenth and fourteenth and fifteenth, sixteenth and seventeenth resistors (R13, R14, R15, R16 and R17) coupled with said first (24, 24') and second (28) electrodes and said low fluid level comparator (I.C.2B), fourteenth and fifteenth resistors (R14 and R15) defining a divider string for applying voltage through said sixteenth resistor (R16) to said first (24, 24') and second (28) electrodes, said thirteenth and seventeenth resistors (R13 and R17) defining a divider applied to a fifth input (5) of low fluid level comparator (I.C.2B), a sixth input (6) of low fluid level comparator (I.C.2B) coupled to sense the voltage across said first (24, 24') and second

(28) electrodes, a second capacitor (C2) presenting a low impedance path to said negative lead for alternating currents, a nineteenth resistor (R19) coupled between said fifth input (5) and the output (7) of said low fluid level comparator (I.C.2B) for providing hysteresis, a second light-emitting diode (L2) and a twentieth resistor (R20) in series between said output (7) of said low fluid level comparator (I.C.2B) and said positive lead (52), a second input (2) to degradation comparator (I.C.2A) being coupled to the output (1) of compensating comparator (I.C.1A) and a third input (3) to degradation comparator (I.C.2A) being coupled to the sixth input (6) to low level comparator (I.C.2B), a third capacitor (C3) disposed between said positive lead (52) and said seventeenth resistor (R17) for power supply decoupling, a third light-emitting diode (L3) and twenty-first resistor (R21) in series between the output (1) of said degradation comparator (I.C.2A) and said positive lead (52).

* * * * *